United States Patent
Kendale et al.

(10) Patent No.: US 8,414,480 B2
(45) Date of Patent: Apr. 9, 2013

(54) METHODS AND DEVICES FOR REDUCING REFLECTION-ILLUMINATED ARTIFACTS

(75) Inventors: Amar Kendale, Newton, MA (US); John Tamkin, San Marino, CA (US); Ethan Post, Pasadena, CA (US)

(73) Assignee: MAQUET Cardiovascular LLC, Wayne, NJ (US)

( * ) Notice: Subject to any disclaimer, the term of this patent is extended or adjusted under 35 U.S.C. 154(b) by 1361 days.

(21) Appl. No.: 12/053,065

(22) Filed: Mar. 21, 2008

(65) Prior Publication Data

US 2008/0255419 A1    Oct. 16, 2008

Related U.S. Application Data

(60) Provisional application No. 60/907,150, filed on Mar. 22, 2007.

(51) Int. Cl.
*A61B 1/06*  (2006.01)
*G02B 6/06*  (2006.01)

(52) U.S. Cl. ......... 600/175; 600/160; 600/176; 385/117

(58) Field of Classification Search ............ 600/127, 600/129, 104, 106, 107, 114–116, 121–125, 600/160–182; 348/65, 68, 77; 385/116, 385/117
See application file for complete search history.

(56) References Cited

U.S. PATENT DOCUMENTS

| | | | |
|---|---|---|---|
| 3,859,539 A | 1/1975 | Allington | |
| 4,961,738 A * | 10/1990 | Mackin | 606/15 |
| 5,193,525 A | 3/1993 | Silverstein et al. | |
| 5,718,663 A | 2/1998 | Wulfsberg | |
| 6,692,430 B2 * | 2/2004 | Adler | 600/109 |
| 8,016,748 B2 * | 9/2011 | Mourlas et al. | 600/115 |
| 2003/0227547 A1 * | 12/2003 | Iddan | 348/151 |
| 2005/0049462 A1 | 3/2005 | Kanazawa | |
| 2006/0036131 A1 * | 2/2006 | Glukhovsky et al. | 600/160 |
| 2006/0226655 A1 | 10/2006 | Smith | |
| 2006/0270900 A1 | 11/2006 | Chin et al. | |
| 2007/0129719 A1 | 6/2007 | Kendale et al. | |
| 2008/0305335 A1 | 12/2008 | Schultes et al. | |

FOREIGN PATENT DOCUMENTS

| | | |
|---|---|---|
| EP | 1803387 | 7/2007 |
| JP | 04295328 A * | 10/1992 |
| WO | WO 2007/004227 | 1/2007 |

OTHER PUBLICATIONS

PCT International Search Report and Written Opinion issued by the EPO in International Application No. PCT/US2008/003729, dated June 24, 2008.

* cited by examiner

*Primary Examiner* — Matthew J Kasztejna
*Assistant Examiner* — Ryan Henderson (57) ABSTRACT

The present disclosure is generally directed towards methods and devices for reducing or eliminating reflection-illuminated artifacts. The methods and devices in several embodiments can include providing a transparent lens cover with a blocking member for reflecting or absorbing internally-reflected light. The lens cover can be attached at the distal end of an endoscope, cannula, and/or lumen in some embodiments. Alternatively, the lens cover can be a permanent part of the endoscope, lumen, and/or cannula.

29 Claims, 9 Drawing Sheets

METHODS AND DEVICES FOR REDUCING REFLECTION-ILLUMINATED ARTIFACTS

CROSS-REFERENCE TO RELATED APPLICATIONS

This application claims priority to U.S. Provisional Application Ser. No.: 60/907,150, entitled "Methods and Devices For Reducing Reflected-Illuminated Artifacts," filed Mar. 22, 2007, the contents of which are incorporated herein by reference.

BACKGROUND OF THE INVENTION

The ability to view internal anatomy has lead to significant advances in surgical capability and diagnosis. In particular, the number of procedures that can be performed in a minimally-invasive manner has increased, while such procedures have, in general, improved patient outcomes and reduced recovery time.

To provide visibility, the distal end of an endoscope can be inserted into the patient through a small hole. Usually, the endoscope is an elongated device that includes a lens at the distal end, and an eyepiece or camera at the proximal end. In addition, a working channel can allow for the delivery of surgical instruments, the collection of samples, and/or implantation of medical devices. Regardless of the configuration, the distal end of the endoscope is fed into the patient to view a surgical procedure and/or to provide observation of patient anatomy for diagnosis. Usually, a light source illuminates an area adjacent to the distal end of the endoscope. In some situations, the light source can be part of the endoscope. For example, the endoscope can include an illumination channel for the passage of light and/or an illumination device. Alternatively, a separate light source can be applied.

While many advances have been made for viewing patient anatomy with an endoscope, improvements in image quality would be beneficial. For example, light reflecting back into the detector can cause reflection-illuminated artifacts. These artifacts can appear as dark or bright ring structures during endoscopic visualization and obscure a portion of the viewing field. Accordingly, improvements to optical devices, such as endoscopes, and particularly improvements to image quality, could facilitate minimally-invasive procedures.

SUMMARY OF THE INVENTION

In accordance with embodiments disclosed herein, devices and methods for reducing reflection-illuminated artifacts are provided.

In one embodiment, a lens cover is described. The lens cover can provide an offset from a detector at the distal end of an endoscope. The lens cover can comprise a first central longitudinal axis and an at least partially transparent wall defining an inner surface and an outer surface. The wall can comprise a proximal end and a distal end, a curvature over at least a portion of the outer surface, a blunt tip at the distal end of the outer surface, and an open interior region. In addition, the wall can be adapted to allow an endoscope to view an object through the distal portion of the lens cover.

The lens cover can further comprise an elongated light-blocking member having a distal end and a proximal end. In one aspect, the blocking member is configured to block and/or absorb reflected light that would otherwise cause a reduction in image quality.

At least a portion of the blocking member can be positioned within the outer surface of the lens cover. For example, the blocking member can extend across a portion of the interior region of the lens cover. In one aspect, the blocking member can extend proximally from the inner surface of the lens cover. For example, the blocking member can extend from the distal inner surface of the lens cover. In at least one embodiment, the blocking member extends less than the full distance of the inner surface of the lens cover.

In one aspect, at least a portion of the blocking member can be positioned along the central longitudinal axis of the lens cover. For example, where the blocking member has an elongate body, the central longitudinal axis of the elongate body can extend along the central longitudinal axis of the lens cover.

In another aspect, the blocking member can have a longitudinal cross-sectional width that converges at the proximal end of the blocking member. For example, the proximal end of the blocking member can include a point or tip. The proximal tip can have a variety of shapes, including, for example, a conical, pyramidal, triangular, or semi-spherical shape.

In yet another aspect, the blocking member can have an open proximal end. In such an embodiment, the cross-sectional width can also converge at the proximal end of the blocking member.

The blocking member can prevent or reduce the transmission of light. For example, the blocking member can be opaque or translucent. In another aspect, the blocking member can be reflective.

In another embodiment the blocking member is used with a medical device. For example, the medical device can comprise a cannula containing a first lumen, the first lumen configured for receipt of an elongated optical device. The device can further include a lens cover comprising a body having an elongated shape, an open inner region, and an outer surface. A transparent distal portion of the body can have a tapered shape and a blunt distal tip. An elongated light blocking member having a distal end and a proximal end can also be included. The distal end of the blocking member can be substantially contained within the outer surface of the lens cover and aligned substantially parallel to the first central longitudinal axis of the lens cover. As used herein, the cannula, lumen, and optical device can all be presented as one inseparable part of a medical device, or can each be independently identifiable parts of the medical device, depending on the embodiment.

In some embodiments, a proximal portion of the lens cover body is adapted to mate with the cannula. In another aspect, the lens cover can mate with the optical device and/or with another portion of the medical device body positioned between the cannula and lens cover.

In an embodiment of the medical device, the cannula can contain a second lumen configured for receipt of a surgical tool. In addition, the medical device described herein can include a light source that provides light to the inner region of the lens cover. For example, the light source can be a light ring. A variety of different light source configurations are possible, including, for example, light directed through the endoscope.

Another device described herein for eliminating reflection-illuminated artifacts can comprise a lens cover having a proximal end, a distal end, and a first central longitudinal axis. Additionally, the device can include a light source adapted to shine light through the lens cover, the light source being located closer to the proximal end of the lens cover than the distal end of the lens cover. A detector can be included for capturing an endoscopic image through the lens cover, the detector being located on the proximal side of the lens cover. Also, the device can include a blocking member attached to the lens cover for blocking light that reflects from the lens cover into the detector, the blocking member having a second central longitudinal axis and being oriented substantially parallel to the first central longitudinal axis of the lens cover.

In another embodiment, methods for making a lens cover that reduces reflection-illuminated artifacts are disclosed. In one aspect, the method can include the steps of forming a transparent lens cover having an elongate body and open interior. A blocking member can be positioned within the open interior of the lens cover and mated therewith.

DESCRIPTION OF THE EMBODIMENTS

Reference will now be made in detail to the present exemplary embodiments, examples of which are illustrated in the accompanying drawings. Wherever possible, the same reference numbers will be used throughout the drawings to refer to the same or like parts.

It is to be understood that both the foregoing background description and the following detailed description are exemplary and explanatory only and are not restrictive. The following embodiments should not be limited to a particular surgery, diagnosis, or procedure type. Similarly, although the user of an embodiment can be referred to as a surgeon, a surgeon is only one type of user capable of using the embodiments herein.

For the purposes of this disclosure, an endoscope can represent any type of imaging device used in a medical procedure. Such endoscopes can generally include an image receiving element, herein referred to as a detector. The detector can include a lens, opening, and/or transparent shield through which an image, in the form of light, is collected. In addition, specific reference to an endoscope is not meant to imply that other parts, such as a device for housing the endoscope, are not present.

An exemplary embodiment described below permits a user, such as a clinician or a surgeon, to attain better visualization while using an endoscope or other camera device to visualize anatomy of a subject. To reduce reflection-illuminated artifacts, an embodiment can include a lens cover with a blocking member.

In accordance with an embodiment of the present invention, the blocking member can increase visualization by reducing the presence of reflection-illuminated artifacts. Such artifacts are primarily caused when light from the endoscopic light source reflects off of a lens cover and into the detector. These reflection-illuminated artifacts can appear as dark ring structures during endoscopic visualization, impairing the surgeon's view of the procedure. The blocking member can reduce or eliminate such reflection-illuminated artifacts and improve endoscope visualization.

Figure 1:
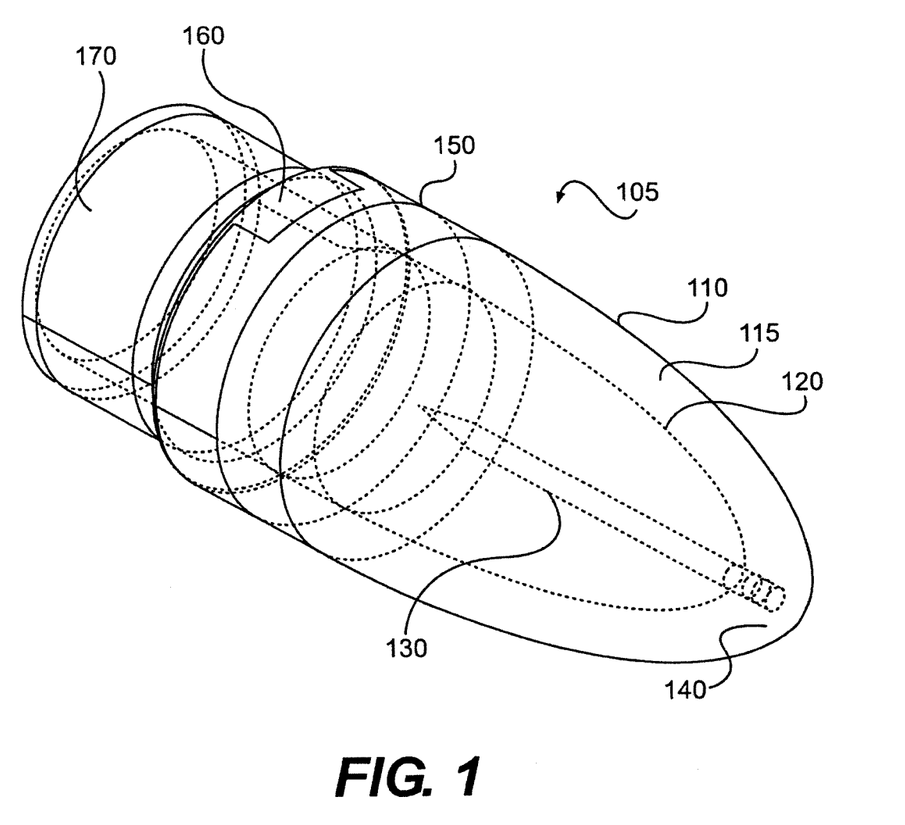
FIG. 1 is an exemplary three-quarters partially-transparent view of a lens cover in accordance with an exemplary embodiment.

FIG. 1 is an exemplary three-quarters view of a lens cover in accordance with an exemplary embodiment. Lens cover 105 is shown with an outer surface 110 and an inner surface 120. The area between 110 and 120 can be thought of as a wall, or the body 115 of the lens cover 105. The inner portion of lens cover 105 can have an open configuration, or alternatively, can include a solid or liquid filing material. Regardless, as described in more detail below, the interior of lens cover 105 can include blocking member 130.

Lens body 115 can have a generally elongate shape with a closed distal end 140 and a proximal opening 170. In one aspect, the distal end 140 has a blunt shape for minimizing patient trauma. Where visualization is required in a sensitive anatomical region, the shape of distal end 140 can reduce the chance of tissue injury. In particular, distal end 140 can have a curved distal outer surface 110. In the example of FIG. 1, the transverse cross-section of lens cover 105 is circular. However, many other cross-sectional lens shapes are possible. For example, the transverse cross-section of the lens cover can be substantially oval or substantially polygonal. In addition, the cross-sectional shape of the lens cover body can vary along the length of the lens cover.

Lens cover 105 can provide an offset between the endoscope (not illustrated in FIG. 1) and the adjacent environment. For example, the body 115 of the lens cover can provide spacing between the endoscope detector and the distal tip of the lens cover. When the lens cover contacts tissue, the offset between the endoscope and the distal end of the lens cover provides spacing so that the tissue surface does not completely block visualization.

Lens cover 105 can be made of a variety of transparent or translucent materials including, for example, various types of polymers, elastomers, and/or glass. The choice of material can depend in part on material cost, strength, optical properties, lens cover size/shape, and/or the intended use of the lens cover.

In one aspect, lens cover 105 allows light to pass through body 115 with minimal or no distortion. In another aspect, the shape of the lens cover can be chosen based on a trade-off between image distortion, the ability to view anatomy through multiple media (e.g., liquid and gas), the desire for a blunt distal tip, and/or lens cover offset. In one aspect, the outer surface of the lens cover can have a curved shape. In another aspect, at least a portion of outer surface 120 has an oblate spheroid shape. In yet another aspect, at least a portion of outer surface 120 has an elliptical shape. Similarly, the inner surface of the lens cover can have curved distal surface. In one aspect, the inner surface of the lens cover has a shape that corresponds to the outer surface of the lens cover.

The proximal portion of lens cover 105 can be configured for mating with an endoscope and/or with a device for housing an endoscope (e.g., a cannula). As shown in FIG. 1, the outer surface of the lens cover can contain a mating feature 160 for attaching to the distal end of a cannula and/or endoscope. For example, a groove, protrusion, and/or thread can facilitate mating. One skilled in the art will appreciate that that the inner and/or outer surfaces of the lens cover can provide a variety of mating surfaces. Exemplary methods and mechanisms for attaching a lens cover 105 to an endoscope or other camera device can include, for example, employing a mechanical interlock, frictional engagement, adhesive(s), heat, and/or other welding and attachment methods and devices. In addition, the lens cover can be permanently or detachably mated with a medical device.

In one aspect, the proximal portion of lens cover 105 is configured to work with a light source in addition to an image detector. For example, as described in more detail below, a light source positioned within or adjacent to lens cover 105 can direct light through the lens cover body.

In addition, or as an alternative to the various exemplary aspect of the lens cover described above, lens cover 105 can include the various features described in the Application entitled METHODS AND DEVICES FOR VIEWING ANATOMIC STRUCTURE and filed even day herewith, the contents of which are incorporated by reference in their entirety.

Figure 2A:
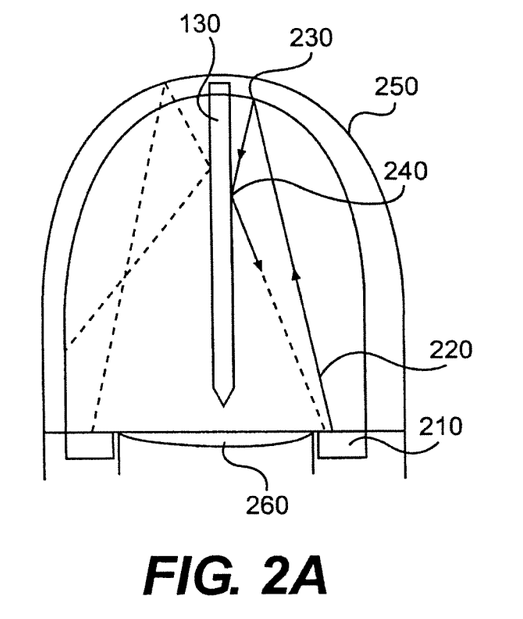
FIG. 2A is an exemplary, isolated, cross-sectional view of the distal end of an endoscope and an attached lens cover, illustrating exemplary light reflection paths within the lens cover in accordance with an exemplary embodiment.

As mentioned above, lens cover 105 can include blocking member 130 for reducing reflection-illuminated artifacts that result when light reflects off of a portion of the lens cover. FIG. 2A is an exemplary isolated, cross-sectional view of the distal end of an endoscope and an attached lens cover, illustrating exemplary light reflection paths within the lens cover in accordance with an exemplary embodiment. As shown, a detector 260 is positioned for viewing from within the interior of lens cover body 250. The detector 260 can be part of the endoscope, such as a lens or camera eye. In some embodiments, the camera portion of the endoscope is located at the proximal end of the endoscope, while the detector 260 is located at the distal end.

In this example, a light source 210 directs light through lens cover 105. In one aspect, the light source is a light ring 210 that generally encircles the endoscope detector 260, illuminating subject anatomy and/or tissue outside the transparent portions of lens cover body 250. Other light sources and light source configurations are possible, such as light sources that have a non-ring configuration or light sources that direct light through detector 260.

Figure 2B:
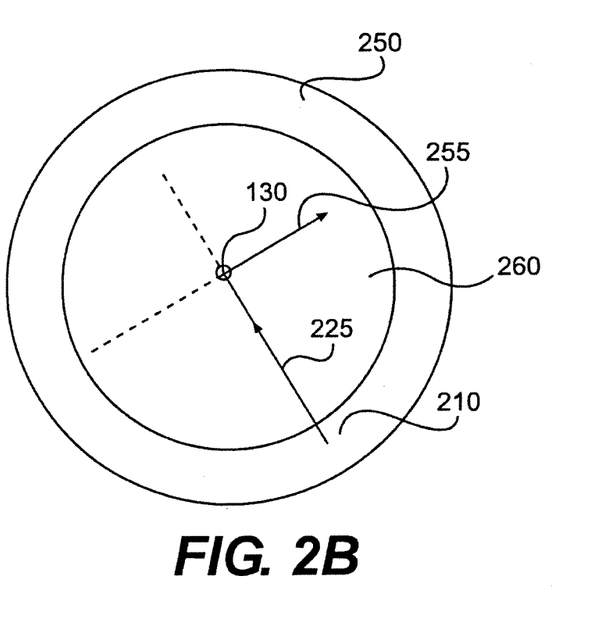
FIG. 2B is an exemplary, isolated, head-on view of the distal end of an endoscope and an attached lens cover, illustrating exemplary light reflection paths within the lens cover in accordance with an exemplary embodiment.

As shown in FIG. 2A, a portion of the light from light source 210, such as light path 220, can internally reflect off of the lens cover 250, such as at point 230. If blocking member 130 were not present, the internally reflected light at 230 would continue into the detector 260. Internally-reflected light captured by the detector can potentially obscure visualization. For example, depending on the detector configuration and/or image processing software, the reflected light can cause dark or bright rings (reflection-illuminated artifacts) to appear in the endoscopic visualization image. One skilled in the art will appreciate that the manner in which reflected light obscures an image (i.e., dark rings, white spots, glare, etc.) is not important, but rather that the use of the blocking member reduces the occurrence of such artifacts. In particular, with blocking member 130 positioned within lens cover 105, a portion of the light that would reflect back to detector 260 is redirected and/or absorbed by blocking member 130. For example, as shown in FIG. 2A, light traveling along path 220 reflects away from detector 260 at 240. A similar example is shown in FIG. 2B, which shows light 225 reflecting away 255 from the detector 260 after being deflected by blocking member 130.

Figure 3A:
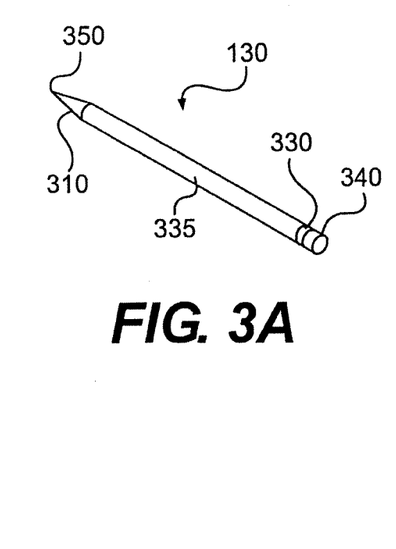
FIG. 3A-B are exemplary illustrations of a blocking member in accordance with exemplary embodiments.
Figure 3B:
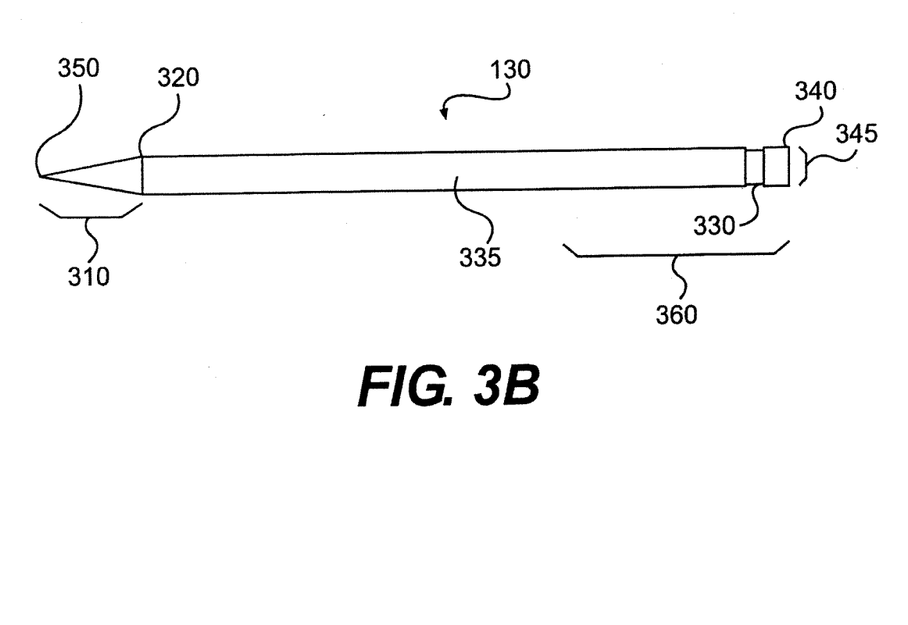

In one embodiment, the blocking member has a generally elongate body 335, at least a portion of which is configured for placement within the lens cover. For example, FIGS. 3A and 3B illustrate blocking member 130, including a proximal portion 310 configured to prevent light from reflecting directly back to the detector and a distal portion 360 for mating with lens cover 105. Between proximal 310 and distal 360 portions, illustrated blocking member 130 has a generally cylindrical cross-sectional shape. However, a variety of alternative shapes are possible for blocking member 130, including, for example, circular, rectangular, oval, triangular, polygonal, and irregular cross-sectional shapes. In addition, while elongate body 335 is illustrated as having a uniform width, the cross-sectional shape and/or width can vary along the length of the blocking member.

The blocking member can be formed of a single, unitary member in one embodiment. In another embodiment, the blocking member 130 can be formed of multiple pieces that are mated together. The blocking member can also have an open interior. For example, the blocking member can have a hollow body similar to a hypodermic tube where the proximal and/or distal ends are open to the interior of the blocking member. In another open-interior embodiment, the blocking member has only one open end.

The proximal portion 310 of blocking member 105 can be configured to prevent light from reflecting directly back to the detector. In one aspect, illustrated in FIG. 4A, the proximal portion of blocking member 110 has a converging longitudinal cross-sectional width, substantially coming to a point at 350. When light source 210 emits light traveling along path 420, the proximal outer surface of blocking member 130 reflects light away from detector 260 at 430 instead of reflecting light back to the detector.

The proximal portion 310 of blocking member 130 can have a variety of light deflecting shapes. In one aspect, illustrated in FIG. 4A, converging proximal portion 310 has a substantially conical shape. Alternatively, proximal portion 310 can have a wedge, pyramidal, or other sloped shape. In addition, the proximal tip need not be centered with respect to the central longitudinal axis of the blocking member. For example, one side of the proximal section can have a steeper slope compared with another side of the proximal section.

In addition, the convergence shown over proximal portion 310 of blocking member 130 can extend over a significantly greater portion of blocking member 130 than depicted in FIGS. 3A and 3B. For example, the entire length of blocking member 130 can include a converging cross-sectional width.

Figure 4A:
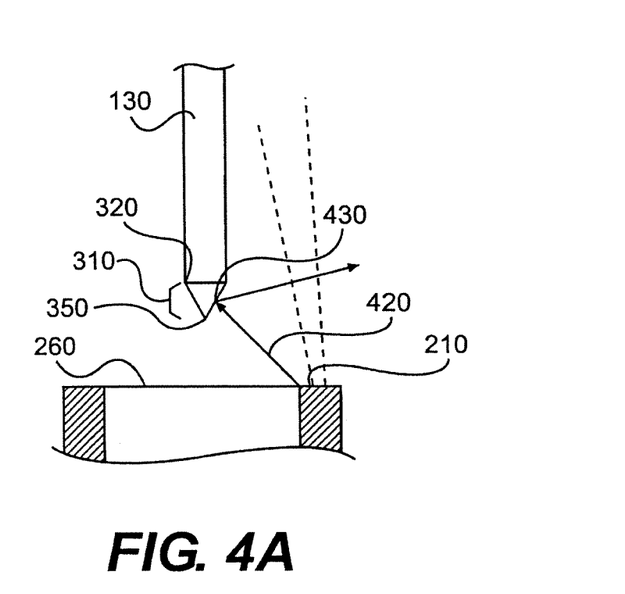
FIG. 4A-B are each exemplary, isolated, partial, longitudinal views of the distal end of an endoscope and respective exemplary blocking members, illustrating light reflection paths with respect to the blocking members and the endoscope detectors in accordance with some exemplary embodiments.

The tapered proximal tip can generally be any angle. However, to reflect the most light away from detector 260, the tip 350 can be angled in a range spanning about 90 degrees or less. The appropriate angle can be affected by the positioning of light source 210 in relation to the proximal portion 310 of blocking member 130, the spacing between the detector 250 and tip 350, and/or the angle at which light is projected from light source 210. Generally, the angle of proximal tip 350 can be in the range of about 1 and 60 degrees. However, angles of less than 1 degree, including very small angles, can also provide excellent light deflection.

In an embodiment, proximal tip 350 converges to a sharp point. The minimal surface area of the sharp point can minimize the amount of light reflected from the tip of the blocking member directly back to the detector. However, the blocking member need not have a sharp point where, for example, there are concerns about sharp surfaces raising the risk of user injury.

Figure 4B:
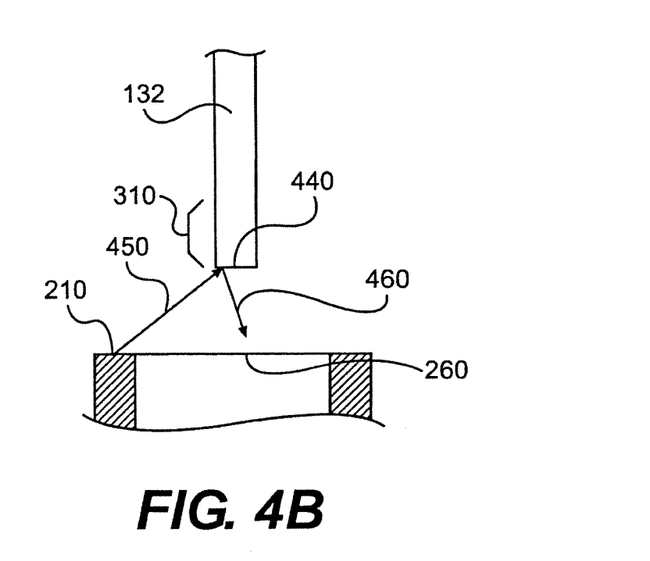

In another embodiment, instead of reflecting light, or in addition to reflecting light, the blocking member can absorb light to reduce the amount of light reflected back to the detector. As shown in FIG. 4B, light traveling along path 450 reaches the proximal portion 310 of the blocking member. Instead of reflecting light back into the detector 260, the light can be absorbed by the proximal surface of the blocking member. In this embodiment, the blocking member may or may not have a tapered proximal portion 310.

As mentioned above, instead of a closed end, the blocking member can include an open proximal end. For example, light can be received in an open interior portion of blocking member 130. The interior surface of the hollow blocking member can reflect light away from the detector and/or can absorb light to reduce reflection to the detector. In this manner, the blocking member 130 can reduce the amount of light reflecting back along path 460 and into detector 260.

The outer surface of an open-ended blocking member 130 can also be tapered at the proximal portion of the blocking member body. For example, the open-ended or hollow blocking member can have a configuration similar to the tapered closed-ended blocking members described above.

As mentioned above, the distal end 340 of blocking member 130 can mate with a portion of lens cover 105. In one aspect, to facilitate mating, the blocking member can include a mating feature. For example, the distal surface of the blocking member can include a groove 330 (as in FIG. 3B). However, in another embodiment the blocking member does not include any surface features adapted for mating with the lens cover. Various methods for positioning and/or attaching the blocking member 130 are discussed in greater detail with reference to FIG. 6C below.

Blocking member 130 can be made from a variety of materials, depending on the intended use of the device. For example, the blocking member 130 can be formed from the variety of conventional biocompatible surgical materials, such as, for example, metals and/or polymers. One skilled in the art will appreciate that a variety of opaque or translucent materials can be used to form the blocking member.

The material of the blocking member 130 can be a reflective. Typically, less diffuse reflection occurs from surfaces commonly thought of as "reflective." For example, the blocking member 130 can have a polished mirror-like outer surface in some embodiments. In particular, the blocking member can be machined or polished to reduce the amount of diffuse reflections occurring along the blocking member 130. For example, polishing the proximal end of blocking member 130 can help to ensure that light reflects in predictable directions from the blocking member 130. However, it should be appreciated that the blocking members need not be polished to effectively reduce reflection-illuminated artifacts.

In another aspect, a light-absorptive material, such as a black-colored material, can reduce or prevent reflection-illuminated artifacts. By absorbing light, the amount of internally-reflected light that finds its way into the detector 260 can be reduced.

Figure 5:
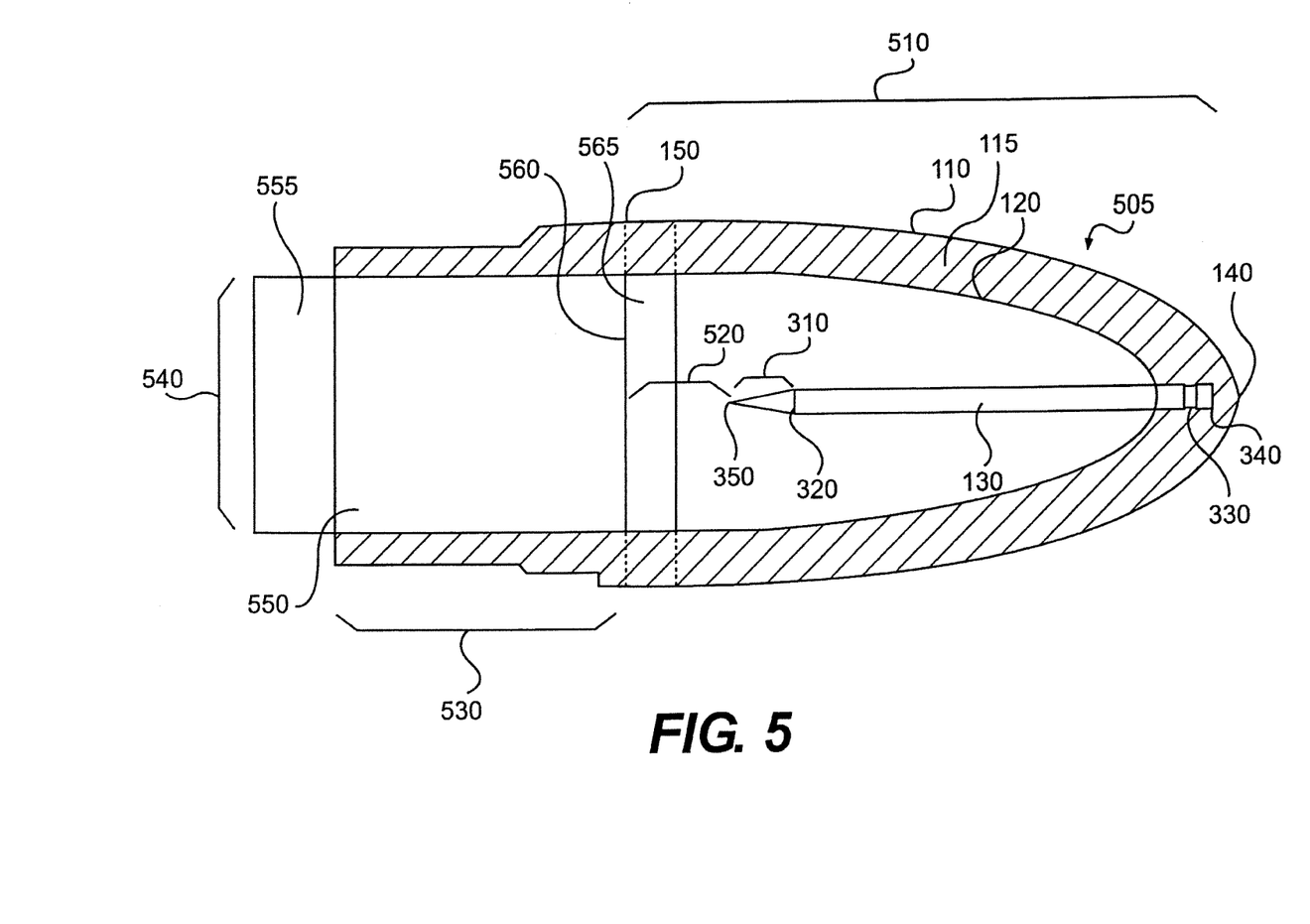
FIG. 5 is an exemplary, isolated, longitudinal, cross-sectional view of an example lens cover with a blocking member in accordance with an exemplary embodiment.

Turning now to FIG. 5, an exemplary isolated, longitudinal, cross-sectional view of a lens cover 505 with a blocking member 130 is depicted in accordance with an exemplary embodiment. Lens cover 505 provides an offset between an endoscope and the distal end 140 of the lens cover body 115. In one aspect, where the endoscope extends into the interior portion of the lens cover, the offset 510 is less than the full length of the lens cover. For example, where the distal end of the endoscope is represented by 150, the offset provided by lens cover 505 can be less than the full length of the lens cover. In one embodiment, an offset in the range of about 8 millimeters to 20 millimeters is provided. In another embodiment, such as when the detector has a wider cone of vision, the offset can be in the range of about 10 millimeters and 14 millimeters.

Generally, blocking member 130 extends for a distance less than the offset, and in one embodiment, the blocking member is sized to provide spacing 520 between the distal end of the detector and the proximal end of the blocking member. Spacing 520 prevents detector 560 from contacting the proximal end of blocking member 130. Where the blocking member has a sharp proximal end 350, spacing 520 can prevent damage to the endoscope and/or user injury.

In another embodiment, the lens cover can incorporate a protective stopper 565 to ensure the detector 560 will not contact blocking member 130. For example, the inner surface of the lens cover can include an area of reduced diameter configured to prevent distal movement of the endoscope with respect to the lens cover. The stopper 565 can be an integrated part of the lens cover 505 and/or be formed by a separate element. Alternatively, or additionally, the proximal end 350 of blocking member 130 can include a soft tip to prevent damage should the endoscope contact the blocking member.

Figures 6A, 6B:
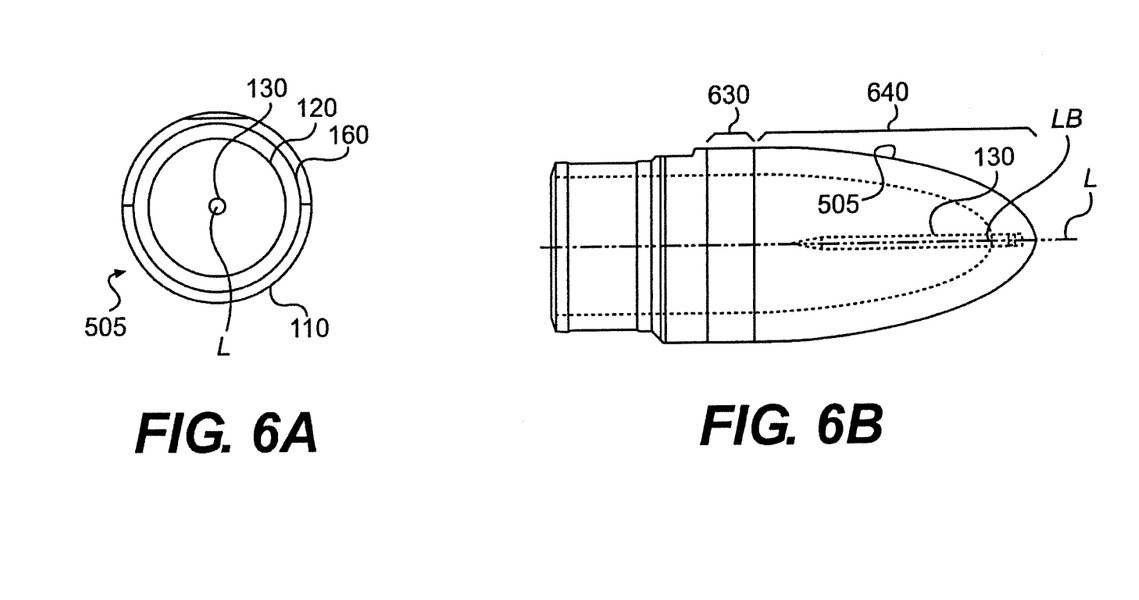
FIG. 6A is an exemplary, isolated, head-on view of the distal end of a lens cover in accordance with an exemplary embodiment.
FIG. 6B is an exemplary illustration of a lens cover with a central longitudinal axis in accordance with an exemplary embodiment.

Depending on the configuration of the light source, lens cover, and detector, the pathway of light reflected to the detector can vary. In one aspect, where the lens cover has a curved distal surface, an illumination axis can fall on along the central longitudinal axis of the lens cover. FIGS. 6A and 6B illustrate the central longitudinal axis L of the lens cover 505. Part of the internally-reflected light that causes reflection-illuminated artifacts crosses (or comes close to crossing) the central longitudinal axis L. Therefore, placing a blocking member 130 along or near the central longitudinal axis L can reduce the reflection-illuminated artifacts. In one such embodiment, the blocking member 130 can be positioned substantially parallel to the central longitudinal axis of the lens cover. In another embodiment, the blocking member 130 is placed such that the central longitudinal axis LB of the blocking member 130 substantially aligns with the central longitudinal axis L of the lens cover 505.

Changing the offset and/or curvature of lens cover 505 can change the pattern of internally reflect light, producing higher intensities of internally-reflected light along different points on the central longitudinal axis L. Thus, the length of the blocking member 130 can be chosen to based on the location of internally-reflected light. In particular, the length of blocking member 130 can be chosen to intersect these high-intensity points.

While the intensity of internally-reflected light varies as a function of distance along the central longitudinal axis L, the highest concentration of internally-reflected light can be near the center of curvature of the lens cover. In the example illustrated in FIGS. 6A-C, the center of curvature is located proximate to the distal, inner surface of the lens cover. The exact location of the center of curvature in other embodiments can be determined by performing a computational optical analysis of the lens cover shape. In one aspect, at least a portion of the blocking member is positioned according to the location of the center of curvature.

Figures 6C, 6D:
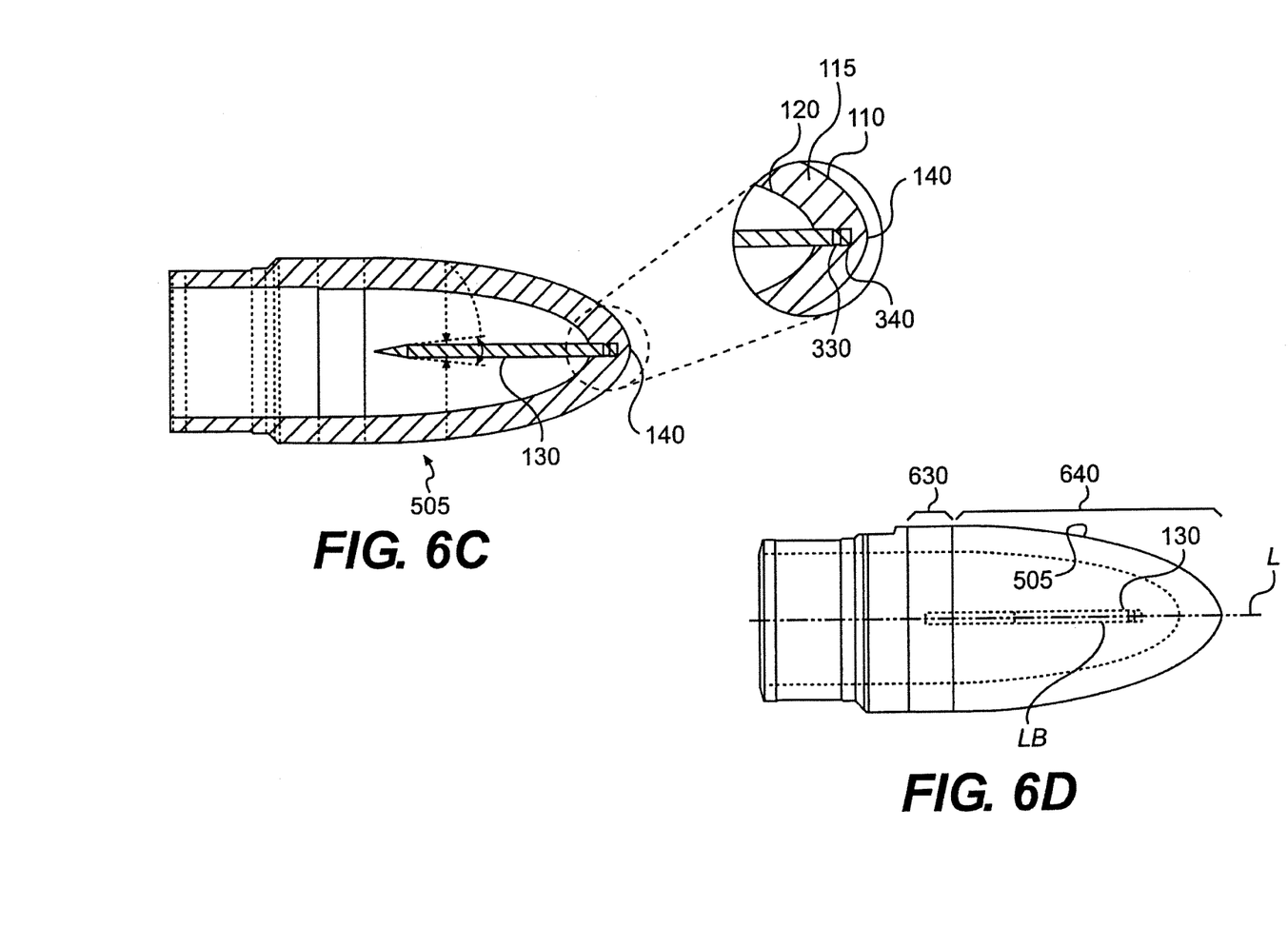
FIG. 6C is an exemplary, isolated, longitudinal, cross-sectional view of a lens cover with a blown up view of an attached blocking member in accordance with an exemplary embodiment.
FIG. 6D is an exemplary illustration of a lens cover with a blocking member attached at the proximal portion of the lens cover in accordance with an exemplary embodiment.

The blocking member can substantially cover only the center of curvature in one aspect. In another embodiment, the blocking member 130 can be configured to cover more than just the center of curvature. This may be beneficial because additional internally-reflected light can pass through the central longitudinal axis L of the lens cover at points other than at the center of curvature.

In the example shown in FIG. 6B, the cross-sectional longitudinal width of the blocking member 130 in this example can be around 0.020 inches. The cross-sectional longitudinal width can vary depending on the shape of the lens cover 505, the location of the light source, and/or the intended use of the lens cover. For example, in cardiac applications, the width can typically be in the range of about 0.001 inches and 0.050 inches, and in another aspect, in the range of about 0.010 inches and 0.025 inches. However, nearly any cross-sectional longitudinal width will work so long as the blocking member can still block light that is crossing near the central longitudinal axis of the lens cover. In this regard, a blocking member 130 with a greater cross-sectional longitudinal width (or diameter) can require less precise placement than a thinner blocking member. However, since the blocking member itself obscures the endoscope's view, minimizing blocking member width also has some tradeoffs.

Depending on the embodiment, various methods exist for attaching a blocking member 130 to a lens cover 505. FIG. 6C is an exemplary isolated, longitudinal, cross-sectional view of a lens cover 505 with a blown-up view of the lens cover and blocking member interface in accordance with an exemplary embodiment.

In one embodiment, the blocking member includes a surface feature or features for mating. For example, the blocking member of FIG. 6C contains a groove near distal end 340. In one aspect, the lens cover can be formed around the groove 330 in blocking member 130. Alternatively, the groove can allow blocking member 130 to mate with lens cover via a snap-fit or interference-fit.

While a groove is illustrated in FIG. 6C, the mating surface feature or features could be a protrusion or bulge. To reduce the impact of the a protruding mating feature on visualization, the protrusion or bulge can be transparent.

A textured surface consisting of roughness at the microscale level (for example, a surface created by grit blasting) can also improve the quality of mating between the blocking element and the lens cover.

In addition, the blocking member does not require surface features to mate with the lens cover in an embodiment. For example, the blocking member can have a smooth outer surface. A frictional and/or adhesive connection between the blocking member and lens cover can provide sufficient hold.

In some embodiments, the blocking member can be substantially contained within the inner region of lens cover 505. In other embodiments, a distal portion of the blocking member 130 can protrude from the distal 140 outer wall 110 of the lens cover 505. In embodiments with a protruding blocking member 130, the distal end 340 of the blocking member 130 can be machined or smoothed to provide a blunt distal surface. In addition or alternatively, an extra protective cover can be placed over the protruding distal end 340 of the blocking member. In some embodiments, this extra protective cover (not shown) can be transparent.

In still another embodiment, the blocking member can mate with the surface of the lens cover without penetrating into the body of the lens cover. For example, the distal most surface of the blocking member can mate with the proximal surface of the lens cover without penetrating the lens cover.

While the illustrated embodiments generally show the blocking member directly mated to the lens cover, in another aspect, an intermediate could be positioned between the blocking member and the lens cover. For example, an intermediate pad can provide a greater surface area for adhesion to lens cover 505. For example, the pad can be positioned along inner surface 120 of the lens cover body 115. The blocking member 130 can be attached to the intermediate pad before or after the pad is attached to the lens cover, depending on the embodiment. In some of these embodiments, the intermediate pad is transparent. In addition, the adhesive used to attach the intermediate pad can be transparent.

While the various embodiments disclosed above generally apply to a blocking member mated to a lens cover via the distal end of the blocking member, mating the proximal end of the blocking member to the lens cover is also contemplated. FIG. 6D is an exemplary illustration of a lens cover with the proximal end of the blocking member attached at the proximal portion of the lens cover. The blocking member mates with a transparent element 630 that rests within the inner region of lens cover 505.

In yet another embodiment, the blocking member can be mated directly to the endoscope, detector, and/or cannula. For example, a detector can have a proximal portion of blocking member 130 mated therewith. In these embodiments, the distally extending blocking member 130 can extend into lens cover 505 when lens cover is attached to the distal portion of the endoscope, cannula, and/or detector.

Figure 7A:
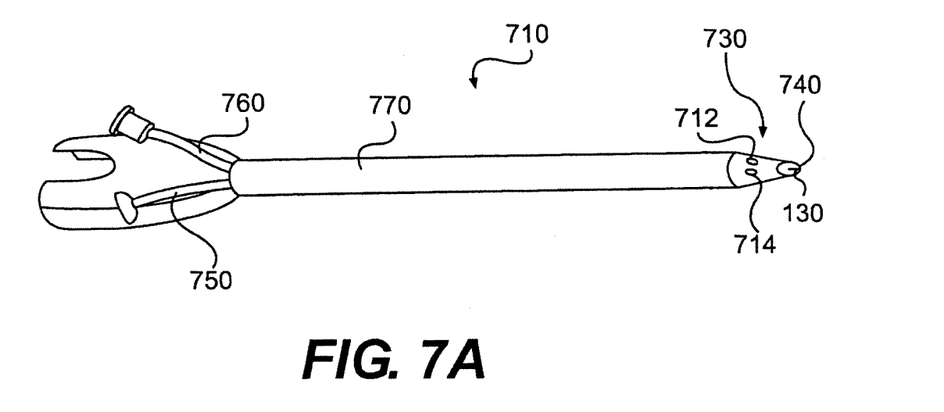
FIG. 7A is an exemplary longitudinal view of a medical device in accordance with an exemplary embodiment.

FIG. 7A is a perspective view of a medical device 710 in accordance with an exemplary embodiment. The medical device 710 can include a cannula 770 extending between a proximal and distal end and housing an optical pathway. A lens cover 740 positioned at the distal end 730 of the cannula 770 allows for visualization via an optical device, such as, for example an endoscope. While the optical device is generally described as a separate element from the body of the medial device, in one aspect, the optical device is incorporated into device 710.

Cannula 770 can also include a first lumen having an open distal end 712 and a second lumen having an open distal end 714. The openings can be at or near the distal end 730 of the cannula 770. While two open-ended lumens are depicted, a single lumen, or more than two open-ended lumens can be used with medical device 710.

In one aspect, a first surgical tool 760 can be housed within the first lumen, while a second surgical tool 750 can be housed within the second lumen. One skilled in the art will appreciate that depending on the intended use of device 710, a variety of tools can be directed through the lumens.

Figure 7B:
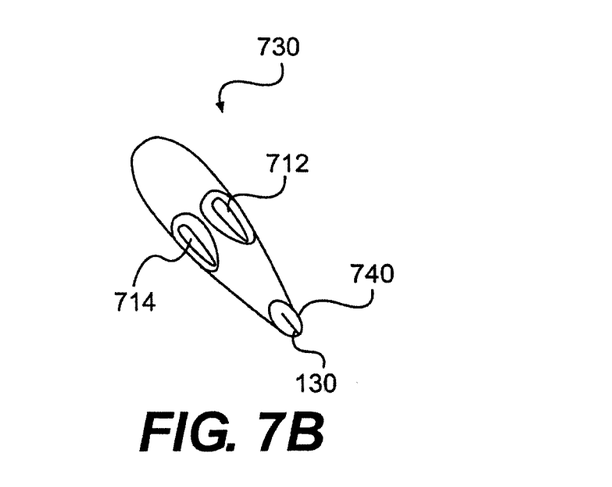
FIG. 7B is an exemplary, isolated, three-quarters view of the distal end of a medical device in accordance with an exemplary embodiment.

The distal end 730 of medical device 710 is depicted in FIG. 7B. As shown, the distal most surface of device 710 is defined by lens cover 740. Where device 710 is used in proximity to sensitive anatomy, the lens cover can provide a blunt distal surface. In one such embodiment, the lens cover has a curved distal most surface. In another aspect, lens cover 740 has an ovular shape, such as an oval of rotation. In still another aspect, the distal portion of lens cover 740 is defined by an elliptical shape.

In another aspect, the lens cover can have a conical shape, or hybrid cross-section with both conical and curved elements. This kind of "sharp" shape is useful for dissection and other similar manipulation of tissue.

In addition, the shape of outer surface 110 may differ from the shape of inner surface 120. This can also be useful in creating a lens cover that functions as a lens in an embodiment. For example, the lens cover can create a magnifying or fisheye effect for use in some applications.

One example of a device used with the blocking element described above is the FLEXVIEW UNILATERAL ROUTING SYSTEM (Boston Scientific Corp., Natick, Mass. (formerly, Guidant Corporation, Indianapolis, Ind.)). The FLEXVIEW is a routing device having an elongate body, endoscope lumen, and working lumens. Lens cover 740 used in conjunction with an endoscope, as well as a routing snare. The FLEXVIEW lens cover 740 can be attached and removed from the endoscope by the user. The routing snare can be looped around and cinched onto the lens cover by the user, and is intended to facilitate placement of a FLEX 10 ablation probe. The endoscope (with the attached lens cover) and snare is inserted through a small hole in the patient's body. The lens cover and endoscope are then used to visualize anatomical structures and position the routing snare as desired. Once in position, the routing snare is used to place the ablation probe, which is used to focus microwave energy on cardiac tissue.

The routing process is visualized through use of the endoscope and the lens cover 740. By employing a lens cover body and a blocking member, as disclosed in various embodiments herein, reflection-illuminated artifacts can be reduced, increasing the quality of visualization throughout the entire procedure. Another example of a device that can be used with the blocking member described herein is the VASOVIEW endoscopic vessel harvesting system is by Boston Scientific Corp., Natick, Mass. (formerly, Guidant Corporation, Indianapolis, Ind.). The VASOVIEW device includes a body having a endoscope channel and one or more working channels for delivery of surgical tools, such as, for example a bisector or scissors. A lens cover can mate with the VASOVIEW body and/or endoscope to allow visualization via the endoscope. In particular, the lens cover can cap the endoscopic channel. More information on some VASOVIEW embodiments can be found in U.S. Pat. Nos. 5,895,353; 5,993,384; 6,176,825; 6,406,425; 6,830,546; 5,595,353; 5,976,168; and 5,980,549, which are incorporated herein by reference.

Figure 8A:
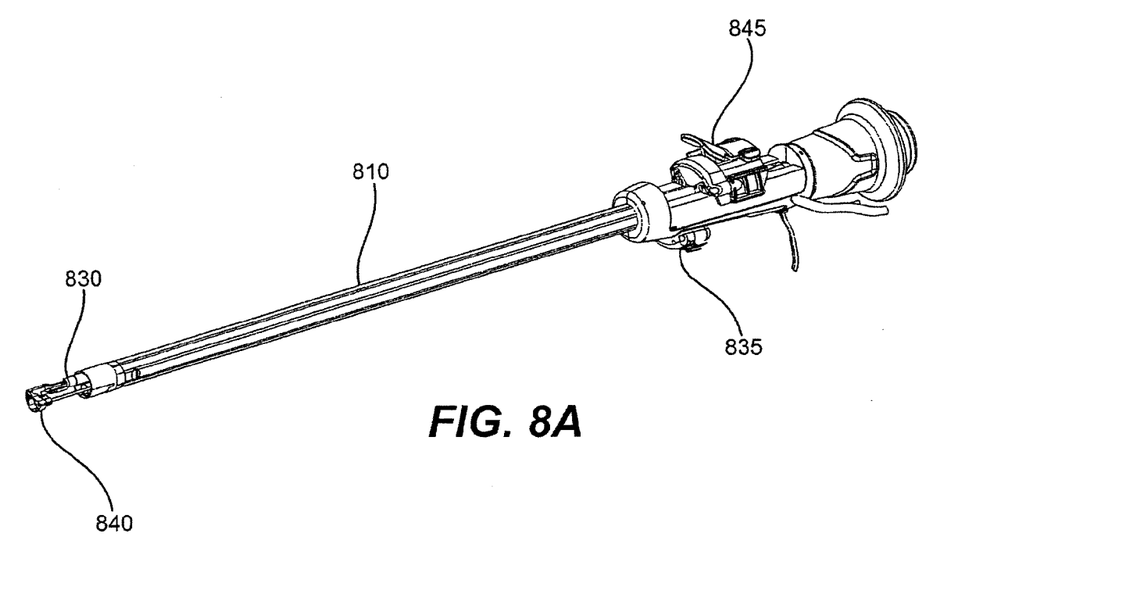
FIG. 8A is an exemplary perspective view of a medical device in accordance with an exemplary embodiment.

FIG. 8A illustrates a perspective view of an example medical device consistent with one embodiment of the VASOVIEW endoscopic vessel harvesting system mentioned above. FIG. 8A shows an example cannula 810 housing a vessel manipulator 840 in an extended position. Cannula 810 includes an outer housing of bioinert material such as polymed UD that may be approximately 12 inches to 18 inches in length. (Other lengths are also possible.) The proximal end of the cannula 810 is disposed in a handle that includes a vessel manipulator actuator, which is coupled to vessel manipulator 112 for controlling the translational movement of vessel manipulator 112. In addition to the vessel manipulator 112, the illustrated cannula 810 houses an endoscope and a bisector tool 130. The handle contains additional tool controls 845 for controlling the bisector tool 830 and/or vessel manipulator 840. Accordingly, the tool controls 845 and vessel manipulation actuator 835 are coupled to the bisector tool 830 and vessel manipulator 840 in some manner to allow for control over those tools.

Figure 8B:
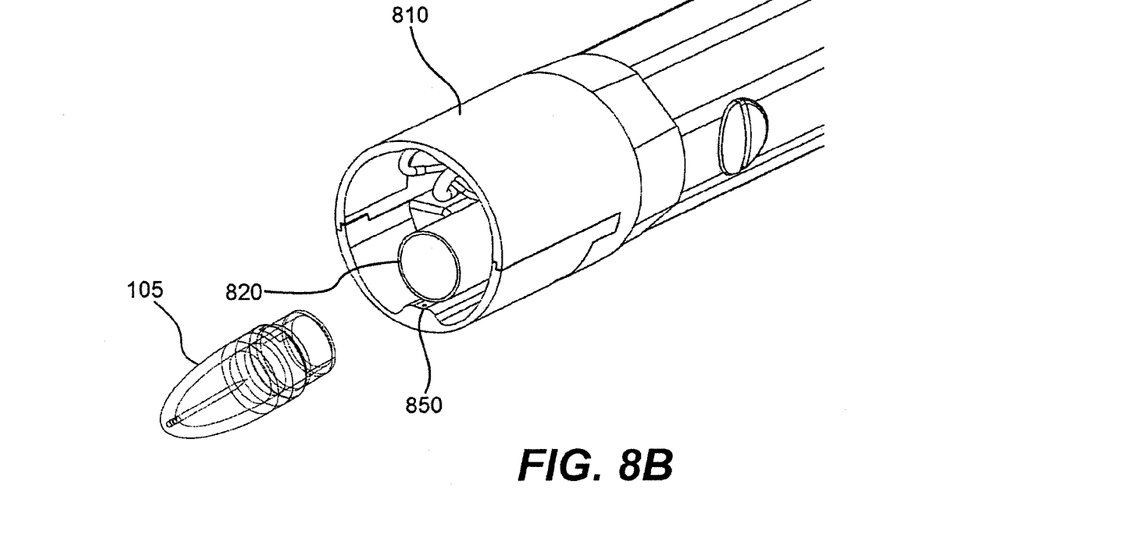
FIG. 8B is an exemplary perspective view of a distal portion of a medical device in accordance with an exemplary embodiment.

FIG. 8B illustrates a perspective view of a distal portion of the example medical device from FIG. 8A. A lumen containing endoscope 820 is housed within cannula 810. However, endoscope 820 may be an integrated part of cannula 810 in one embodiment. A lens cover 105 with blocking member can be attached to the endoscope 820, the lumen, or cannula 810, depending on the embodiment. In another embodiment, the lens cover 105 may already be integrated into the endoscope, lumen, or cannula. In addition to the visual benefits described above, providing a lens cover with a blocking member may facilitate easier tissue separation. An embodiment can include a nozzle 850 for spraying fluid onto the lens cover 105, to cleanse the lens cover of debris that may obscure endoscopic visualization.

Other embodiments will be apparent to those skilled in the art from consideration of the specification and practice of the embodiments disclosed herein. It is intended that the specification and examples be considered as exemplary only, with a true scope and spirit being indicated by the following claims.

What is claimed is:

1. A medical system for viewing internal anatomy, the system comprising:
a lens cover comprising an elongate, rigid body with an open proximal end, an inner surface defining a cavity, and a closed distal end opposing the open proximal end;
a light source adapted to shine light through the lens cover;
a detector for allowing visibility through the lens cover, the detector located relative to the lens cover so as to allow viewing of the inner surface of the lens cover; and
a light blocking member configured as a rod and positioned relative to the lens cover to block at least some of the light from the light source that would otherwise reflect back to the detector, wherein a distal end of the light blocking member projects from the inner surface, the light blocking member extending proximally from the inner surface generally towards the detector.

2. The medical system of claim 1, wherein the lens cover comprises an at least partially transparent wall defining the inner surface and an outer surface of the lens cover, and the lens cover is sized and dimensioned to provide an offset with respect to the detector.

3. The medical system of claim 2, wherein the lens cover further comprises a curvature over at least a portion of the outer surface and a blunt tip of the closed distal end, and -wherein the at least partially transparent wall is adapted to allow the viewing of an object through the at least partially transparent wall at the closed distal end of the lens cover.

4. The medical system of claim 2, wherein the light blocking member is positioned substantially within the outer surface of the lens cover.

5. The medical system of claim 1, wherein the light blocking member is straight throughout its length.

6. The medical system of claim 1, wherein the light blocking member is unitary with the lens cover.

7. The medical system of claim 1, wherein the light blocking member is non-unitary with the lens cover.

8. A medical system comprising:
a light source and detector each located at a distal region of an optical device, the light source is configured for projecting light in a distal direction and the detector is configured to receive images viewed in a distal direction to the detector;
a generally elongate lens cover configured to mate with the distal region of the optical device, the lens cover comprising a closed distal end, an interior surface, an exterior surface, and a sidewall between the interior and exterior surfaces, the sidewall encompassing an interior region that permits light projected from the light source to both (i) pass through the lens cover, and (ii) internally reflect off the lens cover; and
an elongated light blocking member projecting from the interior surface of the lens cover, extending towards the detector in a proximal direction, and terminating at a location distal to and spaced apart from both the light source and the detector, wherein the light blocking member is configured to reduce a quantity of light that can be emitted from the light source, internally reflected off the lens cover, and ultimately received by the detector.

9. The medical system of claim 8, wherein the light blocking member is reflective.

10. The medical system of claim 8, wherein an end of the light blocking member terminating at the location distal to and spaced apart from both the light source is configured as a tapered tip.

11. A medical system comprising:
an endoscope having a proximal end and a distal end, the distal end of the endoscope including a detector for receiving images;
a lens cover operatively associated with the endoscope, wherein the lens cover comprises:
an at least partially transparent wall defining an inner surface and an outer surface of the lens cover, wherein the at least partially transparent wall is rigid and adapted to allow the endoscope to view an object through a portion of the at least partially transparent wall
a proximal end;
a distal end;
a curvature over at least a portion of the at least partially transparent wall outer surface;
a blunt tip located at the distal end of the lens cover and the outer surface of the at least partially transparent wall;
an open interior region; and
an elongated light blocking member having a distal end and a proximal end, the light blocking member extending through at least a portion of a central longitudinal axis of the lens cover, wherein the distal end of the light blocking member projects from the inner surface, the light blocking member comprising an elongate body wherein a length of the elongate body extends proximally from the inner surface generally towards the detector and terminates at a proximal end located distal to the detector, wherein the light blocking member is configured to reflect light, that is reflected from the inner surface, away from the detector.

12. The medical system of claim 11, wherein the light blocking member is positioned substantially within the outer surface of the lens cover.

13. The medical system of claim 11, wherein the light blocking member extends from an area of the lens cover at a distal end of the interior region.

14. The medical system of claim 11, wherein the light blocking member extends less than a full length of the interior region.

15. The medical system of claim 11, wherein the light blocking member has a central longitudinal axis, and the light blocking member is positioned such that the central longitudinal axis of the light blocking member lies substantially along the central longitudinal axis of the lens cover.

16. The medical system of claim 11, wherein the outer surface has an oblate spherical shape over at least the distal end of the lens cover.

17. The medical system of claim 11, wherein the proximal end of the light blocking member is an open proximal end.

18. The medical system of claim 11, wherein the light blocking member is opaque.

19. A medical system for viewing internal anatomy, the medical system comprising:
an elongated optical device having a detector at a distal end thereof;
a cannula containing a first lumen, the first lumen configured for receipt of the elongated optical device;
a lens cover, the lens cover comprising: a body having an elongated shape, a closed distal tip, a central longitudinal axis, an open inner region, and an outer surface having a curved portion, wherein a transparent distal portion of the lens cover body has a tapered shape tapering towards the closed distal tip;
a light source located proximal to the distal tip of the lens cover and adapted to shine light in a distal direction through the inner region of the lens cover; and
an elongated light blocking member to block at least some of the light from the light source that would otherwise reflect back to the detector,
the light blocking member having a distal end and a proximal end, the proximal end of the light blocking member positioned distal to and spaced apart from the light source, the distal end of the light blocking member being substantially contained within the outer surface of the lens cover and aligned substantially parallel to the central longitudinal axis of the lens cover.

20. The medical system of claim 19, wherein the elongated optical device is operatively associated with the lens cover and the light blocking member to allow viewing through the lens cover.

21. The medical system of claim 19, wherein a proximal portion of the lens cover body is adapted to mate with the cannula.

22. The medical system of claim 19, wherein the body is adapted to provide an offset between the optical device and the closed distal tip of the body.

23. The medical system of claim 22, wherein the offset is about 8 millimeters and about 20 millimeters.

24. The medical system of claim 23, wherein the offset is about 10 millimeters and 14 millimeters.

25. The medical system of claim 19, wherein the cannula contains a second lumen, the second lumen is configured for receipt of a surgical tool.

26. The medical system of claim 19, wherein the distal tip is blunt.

27. The medical system of claim 19, wherein the light blocking member comprises a reflective surface and wherein the proximal end of the light blocking member is configured as a conical tip.

28. A medical system for viewing internal anatomy, the system comprising:
a lens cover comprising an elongate body with an open proximal end, an inner surface defining a cavity, and a closed distal end opposing the open proximal end;
a light source adapted to shine light through the lens cover;
a detector for allowing visibility through the lens cover, the detector located relative to the lens cover so as to allow viewing of the inner surface of the lens cover; and
a light blocking member for blocking at least some of the light from the light source that would otherwise reflect back to the detector, wherein the light blocking member has an elongated body and wherein a distal end of the light blocking member projects from the interior surface, the light blocking member extending proximally from the inner surface generally towards the detector and terminating at a proximal end located between the distal end of the lens cover and a distal end of the detector, and wherein the proximal end of the light blocking member is configured as a tapered tip.

29. A medical system for viewing internal anatomy, the system comprising:

a lens cover comprising an elongate body with an open proximal end, an inner surface defining a cavity, and a closed distal end opposing the open proximal end;

a light source adapted to shine light through the lens cover;

a detector for allowing visibility through the lens cover, the detector located relative to the lens cover so as to allow viewing of the inner surface of the lens cover; and a light blocking member for blocking at least some of the light from the light source that would otherwise reflect back to the detector, wherein a distal end of the light blocking member projects from the interior surface, the light blocking member extending proximally from the inner surface generally towards the detector and terminating at a proximal end located distal to and spaced apart from a distal end of the detector.

* * * * *